United States Patent [19]

Sheehan et al.

[11] Patent Number: 5,346,983

[45] Date of Patent: Sep. 13, 1994

[54] SUBSTITUTED PHENYL COMPOUNDS AND PROCESSES FOR PREPARING THE SAME

[75] Inventors: Michael T. Sheehan; James R. Sounik; Bret F. Hann, all of Corpus Christi; William W. Wilkison, III, Richardson, all of Tex.

[73] Assignee: Hoechst Celanese Corporation, Somerville, N.J.

[21] Appl. No.: 70,144

[22] Filed: May 28, 1993

[51] Int. Cl.$^5$ .............................................. C08G 65/38
[52] U.S. Cl. ................................. 528/212; 568/337; 568/608; 568/658; 568/568
[58] Field of Search ............... 568/337, 608, 658, 568; 528/212

[56] References Cited

U.S. PATENT DOCUMENTS

| | | | |
|---|---|---|---|
| 3,721,648 | 3/1973 | Ehrig et al. | 526/284 |
| 4,016,186 | 4/1977 | Kondo et al. | 568/337 |
| 5,064,761 | 11/1991 | Schneider et al. | 435/135 |

Primary Examiner—John Kight, III
Assistant Examiner—R. F. Johnson
Attorney, Agent, or Firm—James J. Mullen; Donald R. Cassady

[57] ABSTRACT

Substituted phenyl compounds endowed with chain extension activity for formulations such as polyurethanes are disclosed, and which have the general formula:

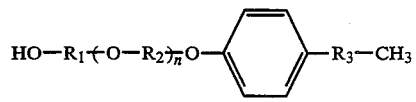

wherein n is 1-1000; $R_1=R_2$, and $R_1$ and $R_2$ are from the group $-CH_2-CH_2$, $-CH_2-C(CH_3)H-$; and $-C(CH_3)H-CH_2-$; and $R_3$ is from the group consisting of:

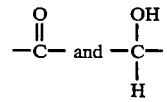

and the diasteromeric salts thereof.

6 Claims, No Drawings

SUBSTITUTED PHENYL COMPOUNDS AND PROCESSES FOR PREPARING THE SAME

BACKGROUND OF THE INVENTION

1. Field of the Invention

The present invention relates to novel derivatives of 4-hydroxyacetophenone (4-HAP) to processes for preparing them, to polymer compositions which contain the novel compounds, and to the use of said compositions for a wide variety of end use applications.

2. Description of Related Art

The following prior art references are disclosed in accordance with the terms of 37 CFR 1.56, 1.97, and 1.98.

U.S. Pat. No. 5,169,848, issued Dec. 8, 1992, to Bettarini et al., discloses new pyridazinones endowed with insecticidal and acaricidal activity.

U.S. Pat. No. 3,520,931, issued Jul. 21, 1970, to d'Ostrowick et al., discloses a process for resolving a mixture of optical antipodes of a primary alpha-arylalkylamine in which one of these antipodes predominates.

U.S. Pat. No. 5,011,996, issued Apr. 30, 1991, to Kiel et al., discloses reaction products of oxo compounds and amines or ammonia, such as α-(p-Chlorophenyl)-ethylamine (Example 1 therein).

U.S. Pat. No. 4,394,496, issued Jul. 19, 1983, to Paul G. Schrader discloses polyglycidyl ethers of this (hydroxyphenyl) alkanes, their blends with other epoxy compounds, and their cured products.

U.S. Pat. No. 4,388,250, issued Jun. 14, 1983, to Farber et al., discloses a process for the preparation of p-Hydroxybenzyl-nitrites (note Table I, columns 7 and 8).

Other U.S. patents which have related application and may be of interest include U.S. Pat. No. 2,298,284; U.S. Pat. No. 3,366,684; U.S. Pat. No. 3,739,026; U.S. Pat. No. 3,225,098; U.S. Pat. No. 3,928,603; and U.S. Pat. No. 5,047,592.

All of the above-cited prior art patents are incorporated herein by reference in their entirety.

Additional Background Information

Compounds belonging to the class of hydroxyacetophenones, processes for preparing the same, and their end use applications are disclosed in U.S. Pat. No. 4,663,485; U.S. Pat. No. 4,524,217; U.S. Pat. No. 4,933,496; and U.S. Pat. No. 4,994,613, the entire disclosures of which patents are incorporated herein by reference.

SUMMARY OF THE INVENTION

The present invention provides novel substituted phenyl compounds ("SPC") endowed with chain extension activity for formulations such as polyurethanes and which have the general formula:

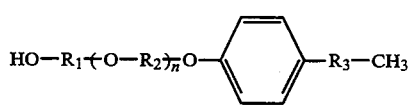

(I)

wherein n is 0-1000; and $R_1$ and $R_2$ are from the group $-CH_2-CH_2-$; $-CH_2-C(CH_3)H-$; and $-C(CH_3)H-CH_2-$; and $R_3$ from the group consisting of:

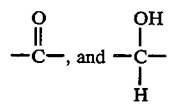

and the diasteromeric salts thereof.

DETAILED DESCRIPTION OF THE PREFERRED EMBODIMENTS

The present invention provides novel substituted phenyl compounds (SPC) which are derivatives of 4-hydroxyacetophenone, a well-known basic building block for numerous organic compounds. These novel SPC's have the general formula as follows:

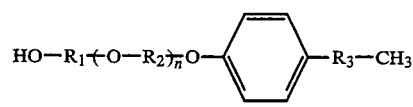

wherein:
n is 0 to 1000 (preferably 0 to 100);
$R_1$ equals $R_2$;
$R_1$ and $R_2$ represent a member from the group:
$-CH_2-CH_2-$
$-CH_2-C(CH_3)H-$
$-C(CH_3)H-CH_2-$; and
$R_3$ is from the group:

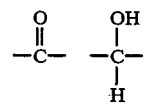

The compounds having the general formula (I) can be prepared by reacting an alkali metal salt of 4-hydroxyacetophenone (4-HAP) with an oxide material such as ethylene oxide or propylene oxide in the presence of a suitable catalyst to form the novel SPC having the above formula (I). This overall reaction scheme using ethylene oxide is shown as follows:

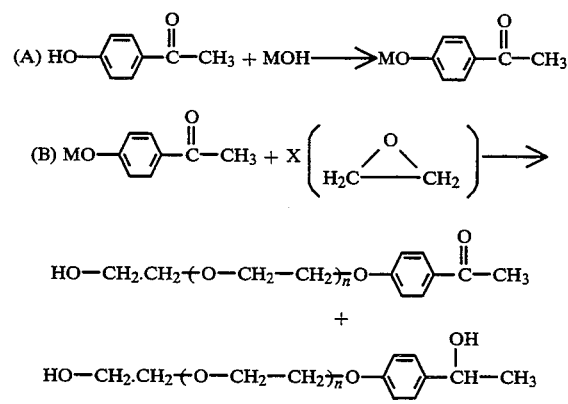

In equation (A), M is an alkali metal such as potassium.

In equation (B), X represents the number of molar equivalents of the ethylene oxide (or propylene oxide) used to form the chain, and n+1 equals X. n can be 0 to 1000, but are preferably from 0 to 100.

In the formulation of the alkali metal salt of 4-HAP, equation (A), the reactants are mixed together in a reaction vessel along with a suitable inert solvent such as isopropanol and then heated at about 30° C. to about 100° C. for a sufficient period of time until all the solids are dissolved into the liquid. The resultant reaction mass is then allowed to cool to room temperature and then the desired alkali metal salt is allowed to crystalize over a period of time suitable to promote crystallization from the solution. The solid material, i.e. the 4-HAP salt, is then separated from the mother liquor by any conventional means, such as filtration. The solid material is then washed with a suitable inert solvent such as heptane and then dried at a temperature of from about 30° C. to about 100° C., under vacuum, where so desired.

In conjunction with equation (B) above, the alkali metal salt of 4-HAP is charged into a reaction vessel along with pre-selected quantities of either ethylene oxide or propylene oxide and a suitable inert solvent such as dimethylformamide (DMF). The reaction vessel is provided with a condenser and a mechanical stirrer. The reaction mass is then slowly heated from room temperature (i.e. 20° C.) to about 100° C. over a period of time to insure that the ethoxylation of propoxylation takes place in the desired fashion. While this part of the process is conducted at atmospheric pressure, it is within the scope of the present invention to conduct this reaction under pressure, e.g. from about 20 psig to about 300 psig, and thus reduce the reaction times. After the reaction has taken place, the reaction mass is allowed to cool to room temperature and then a suitable de-salting agent, such as acetic acid, is added to this mass in order to remove and inactivate the alkali metal ion. This ion complex precipitates and the resultant suspension is separated from the mother liquor by any conventional means such as filtration. This liquid is then reduced under vacuum to an oil, and the oil is then distilled under vacuum and the fraction boiling between 130° C. and 210° C. is collected and represents the desired end product, i.e. the ethoxylated or propoxylated 4-HAP.

Referring to equation (B), it was unexpectedly found that the reaction produces two (2) separate materials which can be recovered by any conventional means such as distillation.

The substituted phenyl compounds (SPC) of this invention are particularly suited for reaction with isocyanates to manufacture articles by a Reaction Injection Molding (RIM) process. RIM is a technique for the rapid mixture and molding of large, fast-curing urethane parts. RIM polyurethane parts are used in a variety of exterior body applications on automobiles where the light weight contributes to energy conservation. RIM parts are generally made by rapidly mixing active hydrogen-containing materials with polyisocyanate and placing the mixture into a mold where reaction proceeds. After reaction and de-molding, the parts may be subjected to an additional curing step which comprises placing the parts in an oven, held at 250° F. or higher.

Surprisingly, it also has been found that the substituted phenyl compounds of this invention are useful as curing agents in forming clear epoxy castings and adhesives with highly satisfactory physical properties. Such epoxy products find application in the electrical and electronic fields. These SPC's also have been found to be suitable for use in polyamides, polyesters, polycarbonates, and epoxy resins.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

Synthesis of Potassium Salt of 4-Hydroxyacetophenone

A mixture of 4-hydroxyacetophenone (556 g), potassium hydroxide (273 g), and isopropanol (3 L) is charged to a 5 L glass reactor fitted with a condenser and mechanical stirrer. The mixture is heated until all of the solids are dissolved (80° C.). The solution is then cooled to room temperature and the product is allowed to crystallize for 12 hours. The solid is isolated by filtration, washed with heptane (1 L), and dried under vacuum (60 torr., 50° C.). The product is a light yellow solid and weighed 610 g (86%). This reaction is representative of equation (A) above.

EXAMPLE 2

A mixture of potassium 4-acetyl phenolate (313 g), propylene oxide (507), and DMF (900 mL) is charged to a 3 L glass reactor fitted with a condenser and mechanical stirrer. The reaction is heated and the temperature slowly increases from 52° C. to 82° C. over a period of 3 hours. The mixture is cooled to room temperature and acetic acid (108 g) is slowly added. The suspension is filtered and the tiltrate is reduced under vacuum to an oil. The oil is distilled under vacuum (0.5 torr.) and the fraction boiling between 140° C. to 205° C. is collected. The product is a clear, colorless liquid and weighs 284 g (63%). Typical physical properties are given in Table I. This reaction is representative of equation (B) above, except that propylene oxide is used instead of ethylene oxide.

TABLE I

| Typical Properties of Propoxylated 4-Hydroxyacetophenone | |
|---|---|
| Property | Propoxylated 4-Hydroxyacetophenone |
| Average n | (wt %) |
| n = 0 | 12.58 |
| n = 1 | 76.08 |
| n = 2 | 11.34 |
| n = 3 | — |
| Molecular Weight (Average) | 251.28 |
| Boiling Range | 140–193° C. (<1 torr.) |
| Density (@ 27° C.) | 1.094 g/mL |
| Color | Clear, Colorless Liquid |
| Solubility (>5 wt %) | |
| Water | No |
| Acetone | Yes |
| Methanol | Yes |
| N,N-Dimethylformamide | Yes |
| Heptane | No |
| Ethyl Acetate | Yes |

EXAMPLES 3–18

Using the procedures set forth in Examples 1 and 2 above, the compounds reported in Table II are obtained. It is inherent that isomers of the propyl group are formed; however, NMR indicates that the indicated compounds are formed.

TABLE II

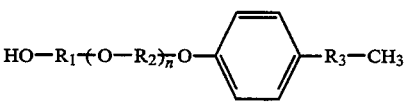

| Example | R₁/R₂ | n(Average) | R₃ |
|---|---|---|---|
| 3 | —CH₂—CH₂— | 2 | —C(O)— |
| 4 | —CH₂—CH₂— | 13 | —C(OH)H— |
| 5 | —CH₂—CH₂— | 81 | —C(O)— |
| 6 | —CH₂—CH₂— | 4 | —C(O)— |
| 7 | —CH₂—CH₂— | 3 | —C(OH)H— |
| 8 | —CH₂—CH₂— | 6 | —C(OH)H— |
| 9 | —CH₂—CH₂— | 10 | —C(OH)H— |
| 10 | —CH₂—CH₂— | 4 | —C(O)— |
| 11 | —CH₂—C(CH₃)H— | 5 | —C(O)— |
| 12 | —CH₂—C(CH₃)H— | 5 | —C(OH)H— |
| 13 | —CH₂—C(CH₃)H— | 9 | —C(OH)H— |
| 14 | —CH₂OC(CH₃)H— | 5 | —C(OH)H— |
| 15 | —CH₂—C(CH₃)H— | 5 | —C(O)— |
| 16 | —CH₂C(CH₃)H— | 11 | —C(O)— |
| 17 | —C(CH₃)H—CH₂— | 3 | —C(OH)H— |
| 18 | —C(CH₃)H—CH₂— | 3 | —C(O)— |

EXAMPLE 19

Synthesis of a Polyurethane with SPC

A 2.0 g sample (0.012 mole) of tolylenediisocyanate (a 80:20 mixture of 2,4 and 2,6 tolylenediisocyanate) is mixed carefully with a 2.9 g sample (0.011 mole) of the SPC prepared according to the procedure in Example 2 above. The mixture thickens and hardens to a glassy resin with the generation of heat. The material is a hard, clear, amber solid and is found to be suitable for use in automobile parts.

EXAMPLES 20–36

Preparation of Polyurethanes Containing SPC

Polyurethanes are prepared incorporating SPC by substitution of SPC for other polyols present in a reaction mixture. Examples are described in the Encyclopedia of Polymer Science & Engineering, Volume 1, pgs. 243–303 (2nd Edition, 1988, Wiley). As used herein, the term, "polyurethane" refers to materials that include the carbamate function as well as other functional groups such as ester, ether, amide, and urea. Polyurethanes are usually produced by the reaction of a polyfunctional isocyanate with a polyol or other hydroxyl-containing reactant. Since the functionality of the hydroxyl-containing reactant or the isocyanate can be adjusted, a wide variety of branched or crosslinked polymers can be formed. The hydroxyl-containing component may be of a wide variety of branched or cross-linked polymers can be formed. The hydroxyl-containing component may be of a wide variety of molecular weights and types including polyester and polyester polyols. The polyfunctional isocyanates may be aromatic, aliphatic, cycloaliphatic, or polycyclic in structure and can be used directly as produced or modified. The flexibility in reactants leads to the wide range of physical properties of available materials. Present invention polymers are prepared by substituting SPC for a portion of the hydroxyl-containing reactant in a mole ratio of SPC/hydroxyl from about 0.001:1 to about 1:1 for the polyol in a polyurethane reaction mixture or, in other words, from about 0.05 to about 50 mole percent of the total mixture as described above in connection with Example 19. Specifically, Example 19 is repeated using the SPC compounds from Examples 3–18. The resultant polyurethane compositions are found functional in a wide variety of automobile parts.

In conjunction with the novel SPC compounds falling within the general structural formula (I) above, each of these compounds contains a chiral carbon atom and, consequently, is a racemate which consists of two mirror-image forms (enantiomers). Where one so desires to provide and/or use only one or single enantiomer thereof, it is within the scope of the present invention that this can be accomplished by means well-known in chirotechnology such as optical resolution by known resolving agents such as optically pure chiral acids. Examples of chiral acids include, without limitation thereof, tartaric acid, molic acid, camphorsulfonic acid, lactic acid, bromocamphorsulfonic acid, mandelic acid, 2-(4-isobutyl-phenyl)-propionic acid (ibuprofen), and derivatives thereof. The use of these chiral acids with the novel SPC provides the diasteromeric salts thereof.

What is claimed is:

1. Substituted phenyl compounds having the structural formula (I):

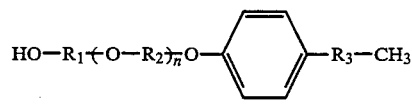

wherein n is 1–1000; R₁=R₂, and R₁ and R₂ are from the group consisting of —CH₂—CH₂—; —C₂—C(CH₃)H—; and —C(CH₃)H—CH₂—; and R₃ is from the group;

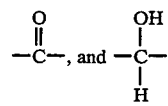

and the diasteromeric salts thereof.

2. Substituted phenyl compounds having the structural formula (II):

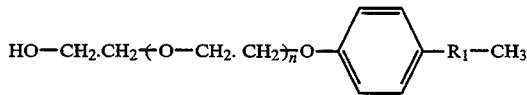

wherein n is 1–1000; and R₁ is from the group consisting of:

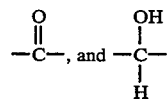

and the diasteromeric salts thereof.

3. Substituted phenyl compounds having the structural formula (III):

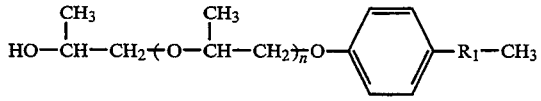

wherein n is 1–1000; and R₁ is from the group consisting of:

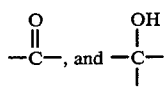
and the diasteromeric salts thereof.
4. Substituted phenyl compounds having the structural formula (IV):
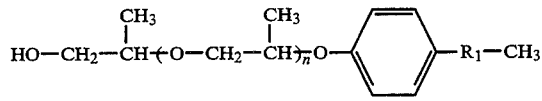
wherein n is 1–1000; and $R_1$ is from the group consisting of:
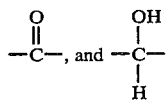
and the diasteromeric salts thereof.
5. The compound as set forth in claim 1 wherein $R_3$ is:
6. The compound as set forth in claim 1 wherein $R_3$ is:
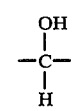
* * * * *

UNITED STATES PATENT AND TRADEMARK OFFICE
CERTIFICATE OF CORRECTION

PATENT NO. : 5,346,983

DATED : September 13, 1994

INVENTOR(S) : Michael T. Sheehan, et al

It is certified that error appears in the above-indentified patent and that said Letters Patent is hereby corrected as shown below:

Column 6, Line 30, after "$-CH_2-CH_2-$; correct $-C_2-C(CH_3)H-$; to read $-CH_2-C(CH_3)H-$;

Signed and Sealed this

Fifth Day of December, 1995

Attest:

BRUCE LEHMAN

*Attesting Officer*       *Commissioner of Patents and Trademarks*